United States Patent [19]
Cox et al.

[11] Patent Number: 5,297,310
[45] Date of Patent: Mar. 29, 1994

[54] CLEANING BRUSH FOR ENDOSCOPES

[76] Inventors: Dennis Cox, 25479 Sheffield La., Saugus, Calif. 91350; Lanita Cox, 25059 Wintergreen Ct., Newhall, Calif. 91381

[21] Appl. No.: 11,468

[22] Filed: Jan. 21, 1993

[51] Int. Cl.⁵ .................. F16L 45/00; A46B 15/00
[52] U.S. Cl. .................... 15/106; 15/104.33; 15/206; 15/104.2
[58] Field of Search ........ 15/104.05, 104.16, 104.165, 15/104.2, 104.33, 106, 114, 118, 164, 165, 206, 211

[56] References Cited

U.S. PATENT DOCUMENTS

| | | | |
|---|---|---|---|
| 4,025,982 | 5/1977 | Palmer | 15/104.2 |
| 4,819,291 | 4/1989 | Gunjian | 15/206 |
| 4,967,439 | 11/1990 | La Londe | 15/104.165 |
| 5,038,509 | 8/1991 | Stephan | 15/104.16 |
| 5,168,593 | 12/1992 | Poje | 15/104.2 |

FOREIGN PATENT DOCUMENTS

| | | | |
|---|---|---|---|
| 72065 | 3/1916 | Switzerland | 15/104.165 |
| 818278 | 8/1959 | United Kingdom | 15/104.16 |

Primary Examiner—Stephen F. Gerrity
Assistant Examiner—Randall E. Chin
Attorney, Agent, or Firm—Donald D. Mon

[57] ABSTRACT

A brush is provided for cleaning endoscope channels which comprises a tubular cannula having a first end and a second end. A wire insert is fitted within the cannula. A first brush having bristles supported on a first core is secured within the first end and a second brush having bristles supported on a second core is secured within the second end. The first core is spaced apart from the wire insert by a distance so as to leave a length of unsupported cannula. A flexible tubular tip is also secured on the first core with a substantial length of the tip free of the core. A depth limit stop having a stop surface thereon is fixed on the cannula spaced from the end of the second core by a distance which prevents the end of the second core from contacting endoscope channels.

2 Claims, 1 Drawing Sheet

CLEANING BRUSH FOR ENDOSCOPES

FIELD OF THE INVENTION

A cleaning brush for endoscope channels and valves.

BACKGROUND OF THE INVENTION

The cross-sections of endoscopes are kept as small as possible because of the constraints of their uses. Very narrow structures often carry several tubular channels which must be cleaned and sterilized after each use. Their valves are manufactured to very close tolerances and are themselves made as small as possible. As a consequence, the cleaning of these expensive instruments is a painstaking procedure.

Conventional brushes for cleaning endoscopes have inherent shortcomings which make their use and the cleaning task unduly troublesome. Many brushes have a tendency to fold back upon themselves rather than to turn into a side channel or a port to clean it. Others expose the instrument to the risk of scratching by the metal core of their bristle brush.

It is an object of this invention to provide a cleaning brush with sufficient columnar strength that it can be pushed into a long channel but is still flexible enough at one of its ends to make the necessary turns, and with guidance means which assures that the turn will be made.

It is another object of this invention to provide at the other end of the cleaning brush a metal-cored bristle brush and a depth-limiting stop, which will prevent the metal core form reaching and scarring inside surfaces of the endoscope.

BRIEF DESCRIPTION OF THE INVENTION

A cleaning brush according to the invention comprises an elongated thin support member. The support member includes a cannula and inside and cemented to the cannula, a stiffly flexible metal insert, preferably braided strands of stainless steel wire.

A bristle brush having a metal core is fitted to a first end of the cannula, with a length of its core cemented into it. At the other end of the core, a stiffly flexible tip extends away from the brush to provide guidance for the brush.

A second brush is fitted to the second end of the cannula. A limit stop is formed on the outside of the cannula to limit the depth to which the second brush can be inserted into the endoscope.

The metal insert extends from the second brush towards the first brush, but terminates a substantial distance from it, so that at the first end of the cannula there is a more flexible end length than in the remainder of the cannula. This enables the cannula to bend to follow a channel, but also to have a strong columnar strength to push and pull it.

The above and other features of this invention will be fully understood from the following detailed description and the accompanying drawings, in which:

DETAILED DESCRIPTION OF THE INVENTION

Figure 1:
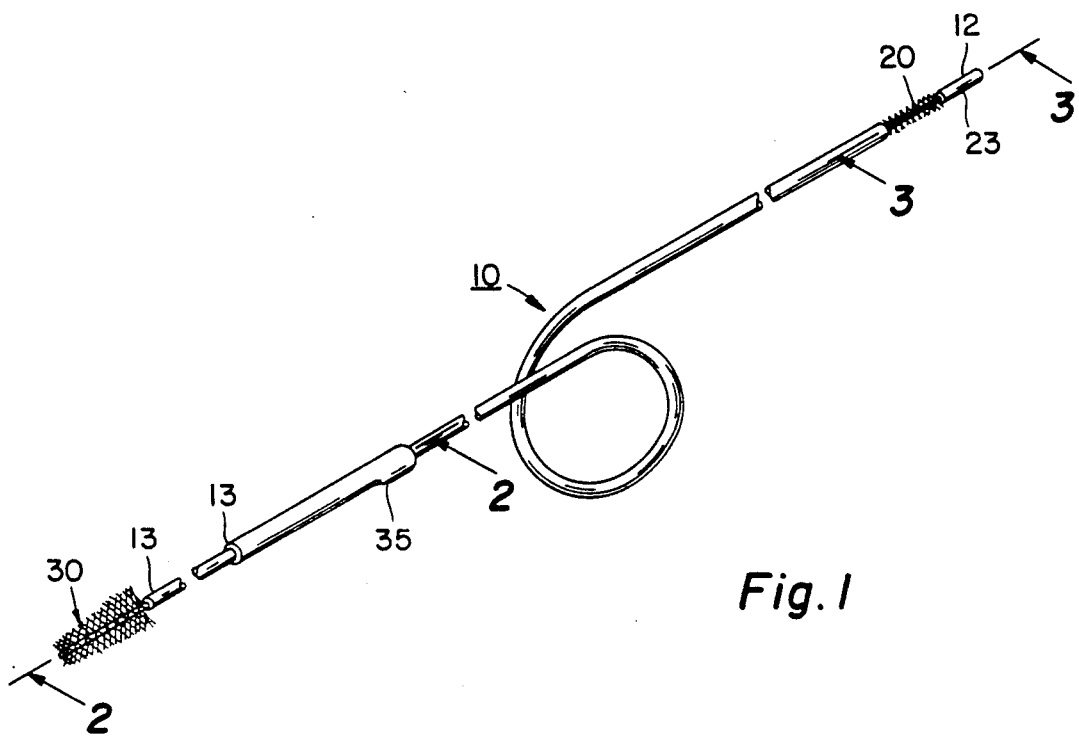
FIG. 1 is a side view, partly in cutaway cross-section, showing the presently preferred embodiment of the invention.
Figure 2:
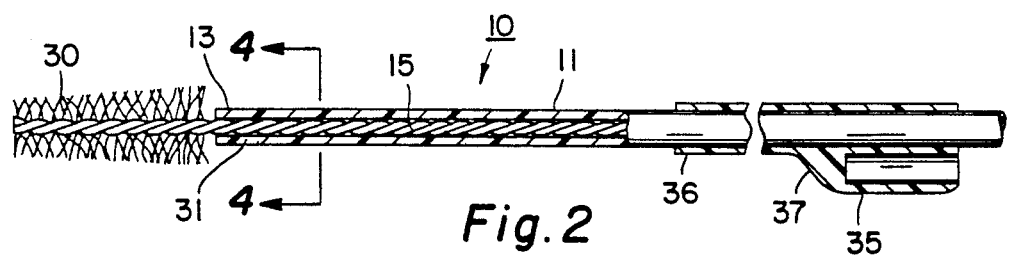
FIG. 2 is a cross-section taken at line 2—2 in FIG. 1.
Figure 3:
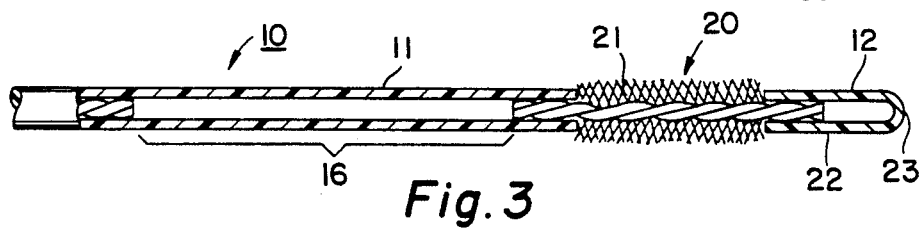
FIG. 3 is a cross-section taken at line 3—3 in FIG. 1.
Figure 4:
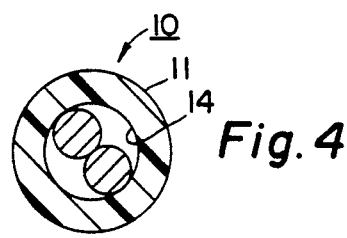
FIG. 4 is a cross section taken at line 4—4 in FIG. 2.

A cleaning brush 10 according to this invention has as its major structure a tubular cannula 11 which extends from a first end 12 to a second end 13. The cannula is conveniently made of polypropylene and has a central passage 14. An outer diameter of 0.062 inches and a wall thickness of 0.025 inches are suitable. The length of the cannula is immaterial, but will usually be between about 160 cm and 240 cm, which provides ample length for gripping the brush for manipulating it.

A wire insert 15 is cemented in the passage. It extends from the second end toward the first end, but terminates a substantial distance from the first end, so as to leave a length 16 of unsupported cannula. Thus, the cannula is stiffly flexible where it is supported by the insert, and more flexible where it is not. The length 16 is still sufficiently strong that it can be pushed into the endoscope, but does provide better flexibility for passage through bends. A length 16 of about 5 inches is usually advantageous. The metal insert is conveniently a braided stainless steel line, such as metal fishing line.

A first brush 20 has a twisted metal core which supports and arranges a plurality of stiffly flexible bristles 21, often nylon. One end of the metal core is without bristles and is cemented into the first end of the cannula. It extends into the cannula just far enough to be retained, so it does not materially reduce the flexibility of the cannula.

At the other end of the metal core there is a closed tubular tip 22 in which just enough of the core is fitted to hold the tip in place. The distal end 23 of the tip is rounded and closed. A substantial length of the tip is flexible material without the core in it. Polypropylene is suitable for this tip. Accordingly this tip is stiffly flexible, but is more flexible than the brush, so that it readily passes through the bends in the endoscope and acts as a guide for the first end, preventing the first end from doubling back on itself. It is safe and does not scratch the endoscope's channels.

At the second end there is a second brush 30. This brush is principally intended to scrub valve seats, valve button channels and lens flushing water nozzles, and its metal core 31 terminates at the end of the brush. Its other end extends into the catheter just far enough to be reliably retained in the catheter. It ends in near adjacency to wire insert 15.

In order to protect the instrument from scratching by the metal core, a depth limit stop 35 is fixed on the cannula. It has a tubular section 36 for attachment to the cannula, and a stop surface 37. Surface 37 is spaced from the free end of the brush by the maximum distance which the brush is to enter into the endoscope. This limitation, when properly placed, prevents the wire core from reaching and scratching a channel of the endoscope.

The use of this brush is evident from the foregoing. When the first end is inserted, the brush has sufficient columnar strength that it can be pushed along. The metal insert gives sufficient strength, both columnar and bending, that it is convenient to handle. The more flexible length 16 provides needed flexibility at the leading end, and the tip provides guidance.

At the second end, the cannula is less flexible than at the first end, so it can be twisted, pushed and pulled. Its depth limitation protects inside surfaces from being scratched.

This invention is not to be limited by the embodiment shown in the drawings and described in the description, which is given by way of example and not of limitation but only in accordance with the scope of the appended claims.

I claim:
1. A brush for cleaning an endoscope comprising:
   a tubular cannula having a first end and a second end, a wire insert fitted in said cannula extending from said second end and terminating a substantial length from said first end;
   a first bristle brush on said first end of said cannula, said first brush comprising a first metal core having first and second ends and a plurality of bristles supported on said first core between said first and second ends of said first core, said first end of said first core extending into said cannula at said first end of said cannula and secured therein, said first end of said first core and said wire insert being spaced apart by said substantial length, and a flexible tubular tip secured to said second end of said first core, with a substantial length of said tip free of said second end of said first core;
   a second bristle brush on said second end of said cannula, said second bristle brush having a second metal core including a free end and a plurality of bristles supported on said free end, said second core extending into said second end of said cannula and secured therein, and a depth limit stop on the exterior of the cannula spaced apart from said free end of said second core of the second bristle brush by a distance which permits said free end of the second core to extend a limited distance into an endoscope channel for cleaning thereof.

2. A brush according to claim 1 in which said tip is closed and rounded at its end farthest from said cannula.

* * * * *